(12) United States Patent
Schulz et al.

(10) Patent No.: US 6,846,965 B1
(45) Date of Patent: Jan. 25, 2005

(54) METHOD FOR THE OLIGOMERIZATION OF $C_2$ $C_8$-OLEFINS

(75) Inventors: Ralf Schulz, Speyer (DE); Marc Walter, Frankenthal (DE); Hans-Peter Neumann, Ludwigshafen (DE); Wolfgang Brox, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/959,792
(22) PCT Filed: May 11, 2000
(86) PCT No.: PCT/EP00/04286
§ 371 (c)(1),
(2), (4) Date: Nov. 7, 2001
(87) PCT Pub. No.: WO00/69795
PCT Pub. Date: Nov. 23, 2000

(30) Foreign Application Priority Data

May 12, 1999 (DE) .......................... 199 22 038

(51) Int. Cl.$^7$ ................. C07C 2/04; C07C 2/02
(52) U.S. Cl. .............. 585/510; 585/311; 585/312; 585/314; 585/315; 585/531
(58) Field of Search ................... 585/311, 312, 585/314, 315, 510, 531

(56) References Cited

U.S. PATENT DOCUMENTS

| | | | | |
|---|---|---|---|---|
| 4,891,457 A | * | 1/1990 | Owen et al. ............... | 585/312 |
| 4,942,021 A | * | 7/1990 | Garwood et al. .......... | 422/194 |

* cited by examiner

Primary Examiner—Walter D. Griffin
Assistant Examiner—Tam M. Nguyen
(74) Attorney, Agent, or Firm—Keil & Weinkauf

(57) ABSTRACT

$C_2$–$C_8$-olefins are oligomerized in a process in which a stream of an olefin-containing hydrocarbon mixture is passed over a heterogeneous, nickel-containing oligomerization catalyst in n successive adiabatically operated reaction zones, where $n \geq 2$, and the hydrocarbon mixture experiences a temperature increase 66 $T_{react}$ in each reaction zone and the hydrocarbon mixture enters the first reaction zone at a temperature $T_{in}$ and before entering each further reaction zone is cooled to a temperature which in each case may be up to 20° C. above or below $T_{in}$, and the relative catalyst volumes of the individual reaction zones are such that the difference in $\Delta T_{react}$ between any two reaction zones is not more than 20° C.

10 Claims, 1 Drawing Sheet

METHOD FOR THE OLIGOMERIZATION OF $C_2$ $C_8$-OLEFINS

Figure 1:
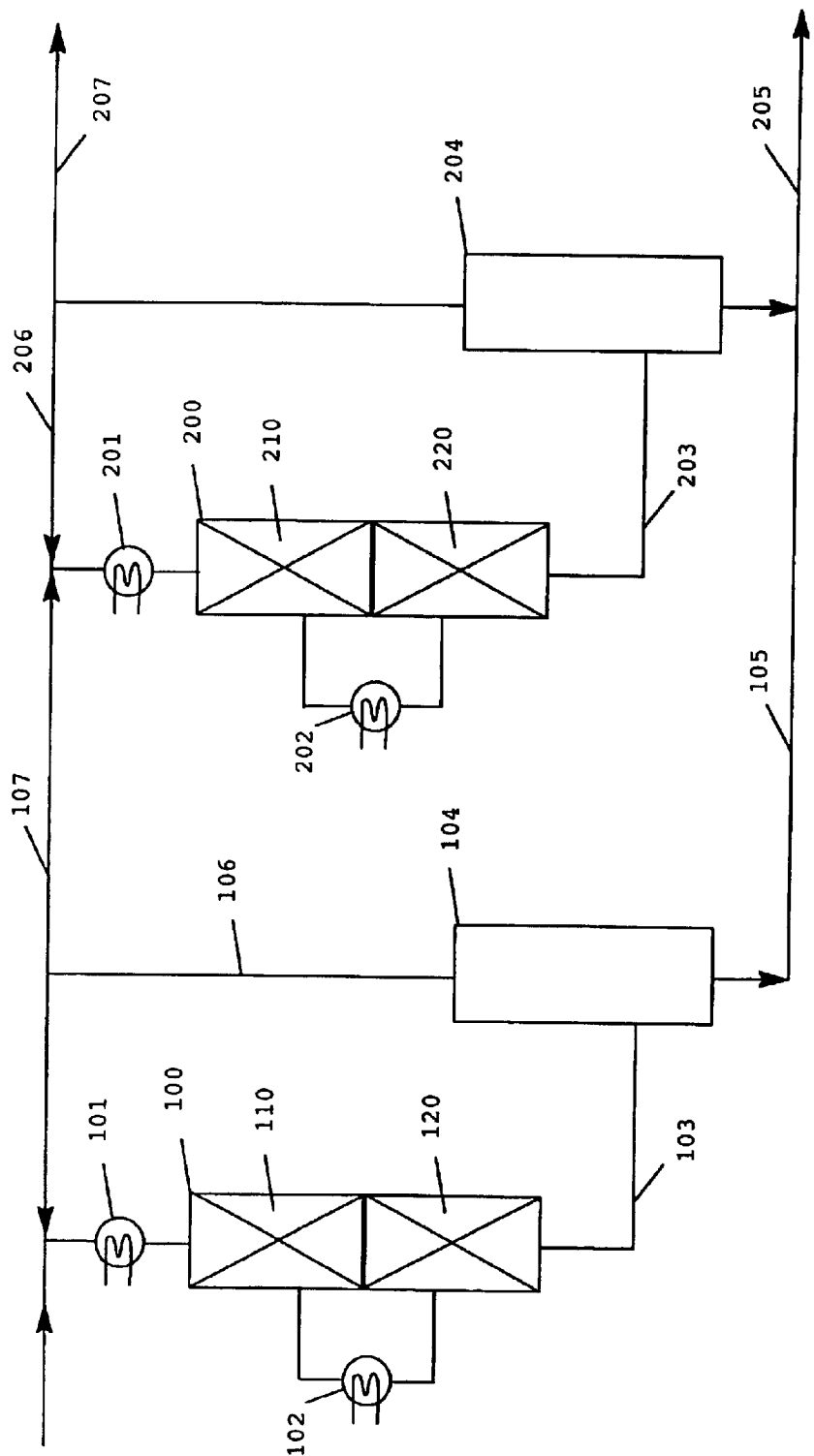

The present invention relates to a process for the oligomerization of $C_2$–$C_8$-olefins in a plurality of successive reaction zones.

Olefins having from 2 to 8 carbon atoms or mixtures thereof are available in large quantities both from FCC (Fluidized Catalyst Cracking) plants and from steam crackers. The use of the $C_4$ fraction, i.e. a mixture consisting essentially of butenes and butanes, if desired after separating off the isobutene, for preparing oligomers, in particular octenes and dodecenes, is known. Both the octenes and the dodecenes can, after hydroformylation and subsequent hydrogenation to the corresponding alcohols, be used, for example, for preparing plasticizers or surfactants.

Oligomerization is carried out industrially using either homogeneous or heterogeneous catalysis. The homogeneously catalyzed process has the disadvantage that the catalyst has to be separated from the reaction mixture. This separation step results in waste streams which have to be worked up, thus incurring costs. In addition, the homogeneous catalyst cannot be regenerated.

The disadvantages described are avoided in the heterogeneously catalyzed olefin oligomerization. The moat important heterogeneously catalyzed olefin oligomerization processes carried out in industry are described, for example, in A. Chauvel and G. Lefebvre, Petrochemical Process, Edition Technip (1989), pp. 183–187 and F. Asinger, Die petrolchemische Industrie, Akademie-Verlag (1971), pp. 278–299.

The oligomerization reaction over a heterogeneous catalyst proceeds exothermically. Owing to the lower capital costs, it is desirable to carry out the olefin oligomerization in adiabatically operated reactors. For the purposes of the present invention, adiabatic reaction conditions are, unlike isothermal reaction conditions in which the heat of reaction generated in an exothermic reaction is removed by cooling by means of cooling or thermostatting devices and the temperature in the reactor is thus kept constant, operating conditions in which the heat liberated in an exothermic reaction is virtually exclusively taken up by the reaction mixture in the reactor and no cooling by means of cooling devices is employed. In the adiabatic operating mode, both the reaction products formed and the heat of reaction are carried away by the stream of reaction mixture passed through the reaction zone. The temperature of the hydrocarbon stream therefore rises along the reactor as the reaction progresses. The temperature difference between exit and entry temperature of the reaction mixture is referred to as the temperature increase.

One possible way of controlling the process is regulation of the entry temperature of the hydrocarbon mixture. To save energy, the hydrocarbon mixture entering the reactor is preferably at a temperature which is as close as possible to ambient temperature. On the other hand, the entry temperature has to be sufficiently high to ensure the desired catalyst activity and reaction rate and thus the conversion sought. Furthermore, the decrease in catalyst activity with increasing operating time has to be taken into account. When the catalyst activity decreases, it is usual to select a higher entry temperature in order to achieve a higher reaction rate and thus to compensate for the decrease in catalyst activity over time. However, the entry temperature cannot be increased at will. The maximum temperature which the hydrocarbon mixture may reach on passing through the reaction zone is limited by safety aspects and practical considerations, for example the maximum pressure for which the plant employed is designed. When the catalyst activity has dropped so far that the hydrocarbon mixture leaving the reaction zone needs to have this maximum temperature, the catalyst is exhausted and has to be replaced by fresh catalyst. The maximum entry temperature is thus determined by the maximum permissible reactor exit temperature minus the temperature increase occurring along the reactor.

The earlier application DE-197 505 31.7 describes a process for preparing octenes and dodecenes by oligomerization of hydrocarbon streams comprising 1-butene and/or 2-butene and butane over a nickel-containing heterogeneous catalyst, where such amounts of the butane and unreacted butene separated from the reaction mixture are recirculated to the oligomerization reaction that the maximum concentration of oligomers in the reaction mixture does not exceed 25% by weight, based on the total reaction hydrocarbon mixture.

It has already been proposed that an adiabatically operated fixed-bed reactor be divided into a plurality of reaction zones, with the reaction mixture being cooled between the individual reaction zones by indirect heat exchange or by mixing in cold gas, cf., for example, M. Baerns (Editor) Chem. Reaktionstechnik, Thieme-verlag, 1987, p. 249.

The earlier application DE 199 15 357.4 describes a process for the oligomerization of $C_2$–$C_8$-olefins over a nickel-containing heterogeneous catalyst, where the catalyst is pretreated by bringing it into contact with a hydrocarbon mixture having a lower olefin content than the feed mixture before it is brought into contact with the feed hydrocarbon mixture. It is stated that the production phase can be carried out in a reactor cascade comprising two or more oligomerization reactors, with the partially reacted reaction mixture being cooled after leaving one reactor and before entering the next reactor of the cascade.

U.S. Pat. No. 4,942,021 discloses a continuous multi-stage process for upgrading a feed comprising lower olefins, in which the feed is passed over an acidic zeolite catalyst in a first reactor, the output from the first reactor is cooled by spraying in water and the mixture of reactor output and water is passed over a metal-containing zeolite catalyst in a second reactor.

U.S. Pat. No. 5,019,357 discloses a two-stage catalytic system for converting a lower olefin feed into heavier liquid hydrocarbons.

The temperature increase occurring in the individual reaction zones is smaller than in a single-zone reactor having the same catalyst volume. The temperature range over which the entry temperature can be varied in order to compensate for the decreasing catalyst activity is therefore higher in this arrangement. The catalyst can thus Ma used over a longer period, which represents a cost advantage.

It has been found that when using nickel-containing oligomerization catalysts with equal division of the catalyst volume into, for example, two reaction zones, the temperature increase in the first reaction zone is considerably higher than in the second reaction zone. The temperature range over which the entry temperature can be varied is limited by the higher temperature increase in the first reaction zone, since the maximum temperature which the hydrocarbon mixture is allowed to reach is reached earlier there than in the second reaction zone. The upper temperature limit can therefore not be exploited fully in the second reaction zone; the catalyst in the second reaction zone is still active while the catalyst in the first reaction zone already needs to be replaced. The catalyst activity in the second reaction zone can therefore not be fully utilized.

It is an object of the present invention to provide a process which allows virtually complete utilization of the catalyst activity.

We have found that this object is achieved by distributing the catalyst volume over the reaction zones so that the temperature increases occurring in the individual reaction zones are virtually equal.

The present invention accordingly provides a process in which a stream of an olefin-containing hydrocarbon mixture is passed over a heterogeneous, nickel-containing oligomerization catalyst in n successive adiabatically operated reaction zones, where $n \geq 2$, and the hydrocarbon mixture experiences a temperature increase $\Delta T_{react}$ in each reaction zone and the hydrocarbon mixture enters the first reaction zone at a temperature $T_{in}$ and before entering each further reaction zone is cooled to a temperature which in each case may be up to 20° C. above or below $T_{in}$, wherein the relative catalyst volumes of the individual reaction zones are such that the difference in $\Delta T_{react}$ between any two reaction zones is not more than 20° C.

The relative catalyst volumes of the individual reaction zones are accordingly such that for all pairs i,j $$|\Delta T_{react}^i - \Delta T_{react}^j| \leq 20° \text{ C.}$$

where $\Delta T_{react}^i$ and $\Delta T_{react}^j$ are the temperature increases experienced by the hydrocarbon mixture in the ith and jth reaction zones respectively, $n \geq 2$, i runs from 2 to n and j runs from 1 to i-1.

$|\Delta T_{react}^i - \Delta T_{react}^j|$ is preferably $\leq 10°$ C., in particular $\leq 5°$ C. In other words, the relative catalyst volumes should be such that the temperature increases in the individual reaction zones lie within a temperature band of 20° C., preferably 10° C., in particular 5° C. The number n of reaction zones is preferably from 2 to 5, in particular 2 or 3.

In order to fulfill the above condition, the catalyst volume of the second and, if present, each further reaction zone is greater than that of the preceding zone, in general from about 30 to 60% by volume greater. In the preferred case of two reaction zones (n=2), the ratio of the catalyst volume of the first reaction zone to the catalyst volume of the second reaction zone is preferably in the range from 30:70 to 45:55 and is particularly preferably about 40:60. When using reaction zones having an essentially uniform cross section, the second and each further reaction zone are accordingly longer than the preceding zones.

The hydrocarbon mixture has a temperature $T_{in}$ when it enters the first reaction zone. Owing to the exothermic reaction in the reaction zone, it leaves the zone at a higher temperature. Before entering a further reaction zone, it is cooled to a temperature which is within 20° C., preferably within 10° C., in particular within 5° C., of $T_{in}$. The hydrocarbon mixture is preferably cooled by indirect heat exchange, usually by means of suitable heat exchangers or the like. It can be advantageous to use a plurality of heat exchangers connected in series which can be switched on or off as required. The injection of coolants or fresh, olefin-containing feed into the partially reacted hydrocarbon mixture is not preferred. Furthermore, it is preferred that the composition of the partially reacted hydrocarbon mixture is not altered between the reaction zones, i.e. it is preferred that no components are separated off or mixed in.

In general, $T_{in}$ has to be higher, the longer the catalyst has been used, in order to compensate for the decreasing catalyst activity over the operating time. $T_{in}$ can, for example, be varied in the range from 20 to 120° C., particularly when using a $C_4$-olefin-containing hydrocarbon mixture. The maximum exit temperature is determined essentially by safety aspects and, in certain preferred embodiments of the invention in which liquid feed mixtures are employed, by the need for the hydrocarbon mixture to be liquid at the pressure selected.

The reaction zones in the process of the present invention are operated adiabatically. For the purposes of the present inventions adiabatic reaction conditions are conditions under which the heat generated in the oligomerization over the heterogeneous catalyst is removed virtually completely by the feed mixture and no cooling by means of cooling or thermostatting devices is employed. It will be understood by a person skilled in the art that a negligibly small part of the heat liberated in the exothermic reaction is unavoidably taken up by the reactor body and given off to the environment by thermal conduction and radiation. In the technical sense, adiabatic reaction conditions therefore refer to an operating mode in which, apart from the part of the heat of reaction passed from the reactor to the environment by means of natural thermal conduction and radiation, all the heat of reaction is taken up by the reaction mixture and is removed together with the latter from the reactor.

The heterogeneous nickel-containing catalysts which can be used may have different structures. It is possible to use catalysts known per se, as are described in C. T. O'Connor et al., Catalysis Today, Vol.6 (1990), pp.336–338. In particular, use is made of supported nickel catalysts. The support materials can be, for example, silica, alumina, aluminosilicates, aluminosilicates having sheet structures and zeolites such as mordenite, faujasite, zeolite X, zeolite Y and ZSM-5, zirconium oxide which has been treated with acids or sulfated titanium dioxide. Particularly useful catalysts are precipitated catalysts which are obtainable by mixing aqueous solutions of nickel salts and silicates, e.g. sodium silicate with nickel nitrate, and, if desired, aluminum salts such as aluminum nitrate, and calcining the precipitate. It is also possible to use catalysts which are obtained by introduction of $Ni^{2+}$ ions into natural or synthetic sheet silicates such as montmorillonites by ion exchange. Suitable catalysts can also be obtained by impregnation of silica, alumina or aluminosilicates with aqueous solutions of soluble nickel salts, e.g. nickel nitrate, nickel sulfate or nickel chloride, and subsequent calcination.

Catalysts comprising nickel oxide are preferred. Particular preference is given to catalysts which consist essentially of NiO, $SiO_2$, $TiO_2$ and/or $ZrO_2$ and, if desired, $Al_2O_3$. Such catalysts are especially preferred when the process of the present invention is employed for the oligomerization of butenes. They lead to preferential dimerization rather than formation of higher oligomers and give predominantly linear products. Most preferred is a catalyst which comprises, as significant active constituents, from 10 to 70% by weight of nickel oxide, from 5 to 30% by weight of titanium dioxide and/or zirconium dioxide, from 0 to 20% by weight of aluminum oxide and silicon dioxide as the balance. Such a catalyst is obtainable by precipitation of the catalyst composition at pH 5–9 by addition of an aqueous solution comprising nickel nitrate to an alkali metal water glass solution containing titanium dioxide and/or zirconium dioxide, filtration, drying and heat treatment at from 350 to 650° C. For production of these catalysts, specific reference may be made to DE-4339713. The full disclosure of this document and the prior art cited therein is hereby incorporated by reference.

The catalyst is preferably in the form of discrete bodies, e.g. in the form of pellets having, for example, a diameter of from 2 to 6 mm and a height of from 3 to 5 mm, rings having, for example, an external diameter of from 5 to 7 mm, a height of from 2 to 5 mm and a hole diameter of from 2 to 3 mm, or extrudates of various lengths having a diameter of, for example, from 1.5 to mm. Such shapes are obtained in a manner known per se by tabletting or extrusion, usually using a tabletting aid such as graphite or stearic acid.

It is possible to use different oligomerization catalysts in the individual reaction zones, although use of the same catalyst in all reaction zones is preferred.

The olefin-containing hydrocarbon mixture used is generally a mixture consisting essentially of olefins and saturated hydrocarbons, although pure olefin streams can also be used. The mixture preferably comprises from 50 to 100% by weight, in particular from 60 to 100% by weight, of $C_2$–$C_8$-olefins, preferably $C_4$–$C_6$-olefins, in particular butenes. When using $C_4$-hydrocarbon mixtures, those having an olefin content of from 50 to 95% by weight, in particular from 60 to 90% by weight, can be successfully employed. The olefin fraction may comprise an individual olefin such as n-hexene or propylene, or a mixture of isomeric olefins such as isomeric butenes, or a mixture of olefins having different numbers of carbon atoms, e.g. mixtures of 3-hexene and 2-pentene, propylene and butene or propylene and ethene. The saturated hydrocarbons present generally have the same number of carbon atoms as the olefin fraction. In many cases it is preferred, with a view to the properties of the oligomerization products, for less than 5% by weight, in particular less than 3% by weight, based on the olefin fraction, of branched olefins to be present in the hydrocarbon mixture used.

A preferred mixture comprises from 50 to 95% by weight, preferably from 60 to 90% by weight, of butenes and from 5 to 50% by weight, preferably from 10 to 40% by weight, of butanes. The butene fraction preferably contains less than 5% by weight, in particular less than 3% by weight, of isobutene (based on the butene fraction). The butene fraction generally has the following composition (in each case based on the butene fraction):

| | |
|---|---|
| 1-butene | from 1 to 99% by weight, |
| cis-2-butene | from 1 to 75% by weight, |
| trans-2-butene | from 1 to 75% by weight, |
| iso-butene | from 1 to 5% by weight. |

A particularly preferred feedstock is raffinate II, which is an isobutene-depleted $C_4$ fraction from an FCC plant or a steam cracker. Raffinate II has, for example, the following composition:

| | |
|---|---|
| i-,n-butane | 30% by weight, |
| i-butene | 2% by weight, |
| 1-butene | 35% by weight, |
| trans-2-butene | 19% by weight, |
| cis-2-butene | 14% by weight. |

The industrially available hydrocarbon mixtures which are suitable as feed mixtures for the purposes of the present invention often contain compounds which act as catalyst poisons and deactivate the oligomerization catalyst. These include oxygen-containing compounds such as alcohols, aldehydes, ketones and ethers and also nitrogen-containing, sulfur-containing and halogen-containing compounds. The presence of such catalyst poisons would lead to an undesirable reduction in the catalyst activity.

According to a preferred aspect of the invention, the hydrocarbon mixture is therefore passed over an adsorbent to remove catalyst poisons prior to being brought into contact with the catalyst. Suitable adsorbents are molecular sieves, preferably those having a pore diameter of from greater than 4 Å to 15 Å. As molecular sieves, it is possible to use crystalline, natural aluminum silicates, e.g. sheet silicates, and also synthetic molecular sieves. Commercial molecular sieves, e.g. those available from Bayer, Dow, Union Carbide, Laporte or Mobil, are also suitable. The molecular sieves can be, for example, zeolites of the A, X and Y types. Further suitable molecular sieves are synthetic molecular sieves which comprise silicon and aluminum as main constituents together with other atoms as secondary constituents. The latter can be incorporated into the zeolite, for example, by ion exchange with the exchangeable cations in the zeolites. Examples which may be mentioned are exchange with rare earths, e.g. gallium, indium or lanthanum, or with nickel, cobalt, copper, zinc or silver. In addition, it is also possible to use synthetic zeolites in which other atoms such as boron or phosphorus have been incorporated into the lattice by coprecipitation.

Further suitable adsorbents are, for example, aluminum oxides, aluminum phosphates, silicon dioxides, kieselguhr, titanium dioxides, zirconium dioxides, polymeric adsorbents and mixtures thereof. The hydrocarbon mixture is advantageously passed over the adsorbent in a fixed bed or a moving bed. While being passed over the adsorbent, the hydrocarbon mixture can be in gaseous or liquid form, but is preferably present as a liquid.

The concentration of oxygen-containing, sulfur-containing, nitrogen-containing and halogen-containing compounds in the hydrocarbon mixture is preferably reduced to less than 1 ppm by weight, in particular less than 0.5 ppm by weight.

If diolefins or alkynes are present in the hydrocarbon mixture, they are preferably removed from the mixture to a residual concentration of less than 10 ppm by weight, in particular less than 5 ppm by weight, particularly preferably less than 1 ppm by weight, prior to the oligomerization. The removal of the diolefins and alkynes can be carried out, for example, by selective hydrogenation, e.g. as described in EP-81041 and DE-1568542.

The oligomerization reaction preferably takes place at from 30 to 280° C., in particular from 30 to 140° C. and particularly preferably from 40 to 130° C., and a pressure of from 10 to 300 bar, preferably from 15 to 100 bar and in particular from 20 to 70 bar. The pressure is advantageously chosen so that the hydrocarbon mixture is in liquid form at the temperature set.

The reaction zones are generally cylindrical reactors which are charged with the catalyst and through which the preferably liquid reaction mixture flows from the top downward or vice versa. The reaction zones can also be configured as sections in a single-piece reactor housing.

After leaving the last reaction zone, the oligomers formed are separated from the unreacted olefins and saturated hydrocarbons in a manner known per se. The oligomers which have been separated off can be purified in a subsequent fractionation step.

In a preferred embodiment of the invention, the maximum concentration of oligomers in the reaction mixture is limited to 30% by weight, preferably 25% by weight and in particular 22% by weight, based on the hydrocarbon reaction mixture. In general, the concentration is not below a lower limit of 10% by weight of oligomers in the reacted reaction mixture prior to it being worked up. This mode of operation enables the selectivity of the oligomerization process of the present invention to be considerably increased in respect of linear oligomers and the catalyst deactivation to be delayed. The limiting of the oligomer concentration can be achieved by reducing the residence time in the reaction zone, i.e. increasing the flow velocity. For this purpose, a substream of the hydrocarbon stream which leaves the last reaction zone and has been freed of the oligomers formed so that it consists essentially of unreacted olefins and/or saturated hydrocarbons is advantageously recirculated to the first reaction zone. The weight ratio of the return stream to fresh hydrocarbon feed stream is, for example, from 0.5 to 10, preferably from 1 to 7, particularly preferably from 1 to 4, in steady-state operation of the reaction system.

It has been found that when the maximum oligomer content of the hydrocarbon reaction mixture is limited as preferred to less than 30% by weight, especially at low olefin concentrations in the hydrocarbon feed mixture, the catalyst volume required to achieve high olefin conversions, e.g. 95% or more, sometimes becomes very large. It has been found that the total catalyst volume can be significantly reduced when the oligomerizatibn process is carried out in a two-stage cascade in which after each stage part of the hydrocarbon stream which has been freed of the oligomers formed in the respective stage is recirculated to a point upstream of the respective stage.

The invention therefore provides, in a further aspect, a process for the oligomerization of $C_2$–$C_8$-olefins, in which a stream of an olefin-containing hydrocarbon mixture is passed over a nickel-containing heterogeneous catalyst in a first reaction stage, the oligomers formed are separated from the hydrocarbon stream after the first reaction stage and the hydrocarbon stream I which has been freed of the oligomers formed is divided into two substreams Ia and Ib, the substream Ia is recirculated to the first reaction stage and the substream Ib is passed over a bed of a nickel-containing heterogeneous catalyst in a second reaction stage, the oligomers formed are separated from the hydrocarbon stream after the second reaction stage and the hydrocarbon stream II which has been freed of the oligomers formed is divided into two substreams IIa and IIb, the substream IIa is recirculated to the second reaction stage and the other substream IIb is discharged from the process, where the ratios of Ia/Ib and IIa/IIb are chosen so that the concentration of oligomers in the reaction mixture does not exceed 30% by weight in any reaction stage.

The above description, particularly in respect of the catalyst used and the hydrocarbon feed mixture, also applies to this aspect of the invention, unless clearly not applicable in this context.

The first and/or second reaction stage advantageously comprises a plurality of successive adiabatically operated reaction zones, as has been described above.

The ratio of the conversion in the first reaction stage as a proportion of the total conversion to that in the second reaction stage is preferably in the range from 1.5:1 to 5:1, in particular from 2:1 to 4.5:1.

The invention is illustrated by the accompanying figure and the following example.

FIG. 1 schematically shows an apparatus suitable for carrying out the process of the present invention. The apparatus comprises two reaction stages (100) and (200) which each comprise two reaction zones (110; 120) or (210; 220). Between the two reaction zones, the reaction mixture is in each case cooled in the heat exchangers (102) and (202), respectively. In the heat exchangers (101) and (201), the hydrocarbon mixture is brought to the respective entry temperature. After leaving the first reaction stage, the reaction mixture is conveyed via line (103) to the distillation column (104) where the oligomers formed are separated off and are taken off via line (105). The unreacted olefins and saturated hydrocarbons are taken off via line (106) and part of this stream is recirculated to the first stage and part is passed via line (107) to the second reaction stage. The ratio of the recirculated stream to the stream passed to the second stage is chosen so that a prescribed concentration of oligomers is not exceeded at the outlet of the reactor (100). The reaction mixture from the second stage is fractionated into oligomers formed and unreacted olefins/saturated hydrocarbons in the distillation column (204). Part of the unreacted olefins/saturated hydrocarbons is recirculated to the second stage via line (206) and part is discharged from the process via line (207). The ratio of the recirculated stream to the discharged stream is chosen so that a prescribed concentration of oligomers is not exceeded at the outlet of the reactor (200).

EXAMPLE

Mathematical Simulation of an Olefin Oligomerization Process

The reaction of a hydrocarbon feed mixture having the composition below over a catalyst which had been produced as described in DE-4339713 in the form of pellets having dimensions of 5 mm×mm (composition in % by weight of the active components: NiO 50% by weight, $TiO_2$ 12.5% by weight, $SiO_2$ 33.5% by weight, $Al_2O_3$ 4% by weight) was simulated by means of the Aspen plus software (Release 9.3) from Aspen Tech, Stanford. The calculations are based on a kinetic model of the reaction which has been set up by mathematical fitting of a large number of experimentally measured data points.

The catalyst volume required to achieve a total conversion of 95% to octenes and dodecenes, based on the butene content of the mixture used, in a 1-stage process and a 2-stage process with different divisions of the total conversion over the two stages (4:1 and 2:1) was calculated. The catalyst volume in the 1-stage process was arbitrarily assigned a value of 100%. Return flows which lead to a maximum concentration of the oligomers formed in the respective reaction stage of 20% by weight in the reaction mixture were employed in the calculations. The results are summarized in the table below.

Composition of the Hydrocarbon Feed Mixture:

| i-butene | 0% by weight, |
|---|---|
| i-butane | 4.87% by weight, |
| 1-butene | 17.15% by weight, |
| cis-2-butene | 16.14% by weight, |
| trans-2-butene | 42.37% by weight, |
| n-butane | 19.48% by weight. |

TABLE

Relative catalyst volumes for achieving a 95% conversion

| 1-stage process | 100% |
|---|---|
| 2-stage process 4:1 | 75% |
| 2-stage process 2:1 | 55% |

We claim:

1. A process for the oligomerization of $C_2$–$C_8$-olefins, in which a stream of an olefin containing hydrocarbon mixture is passed over a heterogeneous nickel-containing oligomerization catalyst in n successive adiabatically operated reaction zones, where n≧2, and the hydrocarbon mixture experiences a temperature increase $\Delta T_{react}$ in each reaction zone and the hydrocarbon mixture enters the first reaction zone at a temperature $T_{in}$, and before entering each further reaction zone is cooled to a temperature which in each case may be up to 20° C. above or below $T_{in}$, wherein the catalyst volume of the second and, if present, each further reaction zone is greater than that of the preceding zone so that the difference in $\Delta T_{react}$ between any reaction zones is not more than 20° C.

2. A process as claimed in claim 1, wherein the difference in $\Delta T_{react}$ is not more than 10° C.

3. A process as claimed in claim 1, wherein used the temperature $T_{in}$ is increased when the activity of the catalyst is low.

4. A process as claimed in claim 1, wherein two reaction zones are used and the ratio of the catalyst volume of the first reaction zone to the catalyst volume of the second reaction zone is in the range from 30:70 to 45:55.

5. A process as claimed in claim 1, wherein $T_{in}$ is in the range from 20 to 120° C.

6. A process as claimed in claim 1, wherein the maximum concentration of the oligomers in the reaction mixture is limited to 30% by weight, based on the hydrocarbon reaction mixture.

7. A process as claimed in claim 6, wherein a substream of the hydrocarbon stream which leaves the nth reaction zone and has been freed of the oligomers formed is recirculated to the first reaction zone.

8. A process as claimed in claim 1, wherein the hydrocarbon stream is in the liquid state.

9. A process for the oligomerization of $C_2$–$C_8$-olefins, in which a stream of an olefin-containing hydrocarbon mixture is passed over a nickel-containing heterogeneous catalyst in a first reaction stage, the oligomers formed are separated from the hydrocarbon stream after the first reaction stage and the hydrocarbon stream I which has been freed of the oligomers formed is divided into two substreams Ia and Ib, the substream Ia is recirculated to the first reaction stage and the substream Ib is passed over a bed of a nickel-containing heterogeneous catalyst in a second reaction stage, the oligomers formed are separated from the hydrocarbon stream after the second reaction stage and the hydrocarbon stream II which has been freed to the oligomers formed is divided into two substreams IIa and IIb, the substream IIa is recirculated to the second reaction stage and the other substream IIb is discharged from the process, where the ratios of Ia/Ib and IIa/IIb are chosen so that the concentration of oligomers in the reaction mixture does not exceed 30% by weight in any reaction stage.

10. A process as claimed in claim 9, wherein the ratio of the conversion in the first reaction stage as a proportion of the total conversion to that in the second reaction stage is in the range from 1.5:1 to 5:1.

* * * * *

UNITED STATES PATENT AND TRADEMARK OFFICE
CERTIFICATE OF CORRECTION

| | |
|---|---|
| PATENT NO. | : 6,846,965 B1 |
| APPLICATION NO. | : 09/959,792 |
| DATED | : January 25, 2005 |
| INVENTOR(S) | : Schultz et al. |

It is certified that error appears in the above-identified patent and that said Letters Patent is hereby corrected as shown below:

Abstract, line 6, "66 $T_{react}$" should read --$\Delta$ $T_{react}$--

Claim 3, column 9, line 13, "wherein used the" should read --wherein the--.

Signed and Sealed this

Twenty-second Day of August, 2006

JON W. DUDAS
*Director of the United States Patent and Trademark Office*